US012181330B2

(12) United States Patent
Hassler et al.

(10) Patent No.: US 12,181,330 B2
(45) Date of Patent: Dec. 31, 2024

(54) APPARATUS AND METHOD FOR THE AUTOMATIC, WEIGHT-DEPENDENT FILLING OF A HOSE SYSTEM

(71) Applicant: FRESENIUS MEDICAL CARE DEUTSCHLAND GMBH, Bad Homburg (DE)

(72) Inventors: Manuel Hassler, Frankfurt am Main (DE); Klaus Wolf, Arnstein (DE); Peter Wabel, Darmstadt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 16/319,594

(22) PCT Filed: Jul. 20, 2017

(86) PCT No.: PCT/EP2017/000887
§ 371 (c)(1),
(2) Date: Jan. 22, 2019

(87) PCT Pub. No.: WO2018/015020
PCT Pub. Date: Jan. 25, 2018

(65) Prior Publication Data
US 2019/0376835 A1    Dec. 12, 2019

(30) Foreign Application Priority Data

Jul. 20, 2016    (DE) .................... 10 2016 008 888.5

(51) Int. Cl.
*G01G 17/06*    (2006.01)
*A61M 1/28*    (2006.01)
*A61M 39/28*    (2006.01)

(52) U.S. Cl.
CPC ............ *G01G 17/06* (2013.01); *A61M 1/288* (2014.02); *A61M 39/28* (2013.01);
(Continued)

(58) Field of Classification Search
CPC ....... G01G 17/06; A61M 1/288; A61M 39/28; A61M 2205/127; A61M 2205/128;
(Continued)

(56) References Cited

U.S. PATENT DOCUMENTS

| 5,445,610 A | 8/1995 | Evert |
| 10,066,983 B2 * | 9/2018 | Groeber ................. A61M 1/28 |

(Continued)

FOREIGN PATENT DOCUMENTS

| DE | 102011018601 | 10/2012 |
| DE | 102015010467 | 2/2017 |

(Continued)

*Primary Examiner* — Quynh-Nhu H. Vu
(74) *Attorney, Agent, or Firm* — Kilyk & Bowersox, P.L.L.C.

(57) ABSTRACT

A method and an apparatus are provided for the automatic, weight-dependent filling of a hose system, in particular for a gravimetric cycler for peritoneal dialysis, having only one scale. The hose system includes at least three line sections for connection to at least one drainage bag, to at least one solution bag and to a patient. The method includes opening at least one bag valve and at least drainage: valve, and deriving a first opening duration of the valves from a weight of the solution bag measured by means of the scale and from at least one characteristic.

15 Claims, 4 Drawing Sheets

(52) U.S. Cl.
CPC .............. *A61M 2205/127* (2013.01); *A61M 2205/128* (2013.01); *A61M 2205/18* (2013.01); *A61M 2205/3393* (2013.01); *A61M 2205/502* (2013.01); *A61M 2205/581* (2013.01); *A61M 2205/587* (2013.01); *A61M 2209/084* (2013.01)

(58) Field of Classification Search
CPC ...... A61M 2205/18; A61M 2205/3393; A61M 2205/502; A61M 2205/581; A61M 2205/587; A61M 2209/084; A61M 1/1603; A61M 1/1617; A61M 1/28; A61M 1/0011; A61M 1/0058; A61M 1/14; A61M 1/287

See application file for complete search history.

(56) References Cited

U.S. PATENT DOCUMENTS

| | | | |
|---|---|---|---|
| 2005/0126998 A1* | 6/2005 | Childers | A61M 1/3621 210/646 |
| 2007/0276328 A1* | 11/2007 | Childers | A61M 1/0023 604/131 |
| 2020/0179584 A1* | 6/2020 | Wabel | A61M 1/287 |
| 2024/0016990 A1* | 1/2024 | Wolf | A61M 1/282 |

FOREIGN PATENT DOCUMENTS

| | | |
|---|---|---|
| DE | 102016008888 | 1/2018 |
| WO | WO.2013/067359 | 5/2013 |

* cited by examiner

APPARATUS AND METHOD FOR THE AUTOMATIC, WEIGHT-DEPENDENT FILLING OF A HOSE SYSTEM

BACKGROUND OF THE INVENTION

Field of the Invention

The invention relates to an apparatus and to a method for the automatic, weight-dependent filling of a hose system, in particular for a gravimetric cycler for peritoneal dialysis having only one scale, wherein the hose system comprises at least three line sections which are configured for connecting the hose system to at least one drainage bag, to at least one solution bag and to a patient.

Description of the Related Art

It is particularly important before the start of dialysis treatments that the lines of hose systems used in the process are free of air and are filled. This is achieved by the flushing and filling of the hose or of the hose system with dialysis fluid. For this purpose, where possible, only so much dialysis solution should be consumed as is necessary to flush the air from the system and to fill the hose with fluid. Since both the dialyzate containers and the dialysis solution are transparent as a rule and since the fluid flows comparatively fast through the hose system, this can only be carried out while observing a very short response time for a safe application and an efficient use of the dialysis solution for the flushing process.

The terms "flushing" and "filling" represent synonyms within the framework of the invention.

Apparatus and/or methods are known from the prior art which work, for example, with a central processor which is connected to a weighing device and to a clock to be able to track the filling time, dwell time and drain time. Systems having only one scale are known in this respect. The filling phase and the drain phase, however, never take place at the same time so that the use of a single weighing device is sufficient. Flushing processes which can be controlled automatically and can be detected via a weight balancing using only one scale are unknown in this respect.

No apparatus or methods are known from the prior art which work with a characteristic which controls the opening time of the valves in dependence on the weight in conjunction with only one scale or load cell for the flushing of the hose kit, in particular with gravimetrically operating units in peritoneal dialysis. With the apparatus in accordance with the invention, the changing weight reduction during the fluid drain in the flushing process is taken into account, which is likewise not known from the prior art. Nor are any apparatus or methods known from the prior art which allow a recognition of the proper opening of the bag clamps or hose clamps.

The term "bag" within the framework of the present invention stands for any desired containers, irrespectively of whether they have rigid and/or flexible walls.

SUMMARY OF THE INVENTION

Against this background, it is the object of the invention to provide an improved apparatus and an improved method respectively for flushing a hose system in which a complete filling with dialysis fluid is ensured and in so doing the dialyzate quantity can be portioned better or more accurately. Only the actually required quantity of dialyzate should hereby be used for flushing the hose lines. It is a further object of the invention to enable a proper check of dialyzate bag connectors and/or hose clamps or of corresponding valves, whereby patient safety and operating comfort are increased.

This object is achieved in accordance with the invention by a method for the automatic, weight-dependent flushing or filling of a hose system, in particular for a gravimetric cycler for peritoneal dialysis, having only one scale, wherein the hose system comprises at least three line sections for connection to at least one drainage bag, to at least one solution bag and to a patient, wherein furthermore at least one bag valve and at least one drainage valve are opened and a first opening duration of the valves is derived from the weight of the solution bag measured by means of the scale and from a characteristic.

The term of solution bag can in this respect comprise one individual solution bag or a plurality of solution bags. The opening duration which can be derived from the characteristic can in this respect relate to the opening duration of one valve or of both valves. It is also conceivable that different opening durations for the individual valves are stored. The bag valve and the drainage valve can be meant by the valves that are opened. In accordance with the method, a regulation/control can be present which can be coupled to the scale and which can detect the solution bag or its weight. Furthermore, in accordance with the method, the characteristic can be made use of which may, for example, be implemented and/or stored in the regulation/control. The regulation/control can thus compare the measured weight of the solution bag with the stored characteristic and can determine a first opening duration for which the valves should be open from the characteristic. The weight of the solution bag in this respect makes it possible to find a good approximation value for the time which is required to fill the hose system with dialyzate solution.

It is also conceivable in this respect that the air pressure and/or the unit height are taken into account in the preparation of the characteristic.

It is conceivable in a preferred embodiment that it is detected by means of the scale whether the valves have been opened. To determine whether a malfunction of at least one of the valves is, for example, present despite a corresponding opening signal to the valves, the weight of the solution bag can furthermore be detected during the opening phase of the valves by means of the above-mentioned regulation/control. If it is detected in this respect that no reduction in the weight of the solution bag has been detected despite an output signal to open the valves, this can be interpreted as an indication of a malfunction of at least one of the valves or a conclusion can be drawn on an incorrectly set up system and this can be detected and/or displayed by the regulation/control. In accordance with the method, an indication can be output to an operator, for example via a display or light emitting diode or via an acoustic signal.

It is conceivable in a further preferred embodiment that a weight reduction of the solution bag is detected by means of the scale during the opening duration of the valves and the first opening duration is modified in dependence on the detected weight reduction. A second, corrected opening duration is hereby calculated. If it is, for example, determined during the opening duration of the valves that the weight of the solution bag is falling too slowly or too fast, the first opening duration of the valves can be correspondingly extended or shortened. It can be taken into account in this respect whether the weight reduction of the solution bag comes close to or reaches a stored desired weight reduction.

If this is not the case, the opening duration can be modified or extended accordingly such that the desired weight reduction is achieved. Conversely, on a determination of a fast weight reduction or a fast approximation to a desired weight reduction, the first opening duration can be shortened such that, where possible, no larger weight reduction than the desired weight reduction occurs. The second opening duration can thus also be shorter than the first opening duration.

It is further conceivable in a further preferred embodiment that, after closing the valves, a prompt is issued to an operator to open a hose clamp and that hereby dialysis fluid is conducted in the direction of a connector. The hose clamp can in this respect be a third valve which acts on the hose system and can, for example, be configured as manually operable by the operator. It is possible by the opening of the hose clamp to connect the hose system to a patient access or to a patient line. The operator can in particular be a patient who is preparing a peritoneal dialysis.

Provision can furthermore be made in a further preferred embodiment that it is detected by means of the scale whether the hose clamp has been opened. If, for example, a prompt has been output to an operator to open the hose clamp and if, subsequent thereto, no reduction of the weight of the solution bag is detected, this can be interpreted in accordance with the method as an indication that the hose clamp is still closed. A corresponding indication to the operator or a corresponding warning message can accordingly be output to open the hose clamp for flushing through the corresponding hose section.

A weight-dependent filling process can also be provided in a further embodiment. A smaller length of time is then provided for the opening of the valves for such a refilling.

The invention is furthermore directed to an apparatus for the automatic, weight-dependent filling of a hose system, in particular for a gravimetric cycler for peritoneal dialysis, having only one scale, wherein the hose system comprises at least three line section for connection to at least one drainage bag, to at least one solution bag and to a patient, wherein the apparatus comprises a regulation/control in which at least one characteristic is stored which indicates valve opening durations in dependence on the weight of a solution bag. The solution bag can be a container for a dialyzate solution and the valve opening durations can be the same or different for both valves.

The apparatus can in this respect be configured in a preferred embodiment for opening at least one bag valve and/or drainage valve in dependence on the weight of the solution bag. The opening of the valves can in this respect take place automatically, with the valves being controllable accordingly via the regulation/control.

It is furthermore conceivable in a further embodiment that the regulation/control is configured to verify the correct opening of the bag valve and/or drainage valve with reference to a detected weight change. A correct opening of the valves is present when the valves have also been opened in response to a corresponding signal of the regulation/control. This can be determined in that a corresponding weight reduction of the solution bag is detectable on the presence of a correct opening. If this is not the case, this is to be interpreted as an indication of an incorrect opening of the valves and a corresponding warning signal can be output. Conversely, on a correct opening of the valves, an actuation signal can be output. The corresponding verification hereby takes place.

Provision can be made in a further preferred embodiment that the apparatus comprises an output device which is configured for outputting information to an operator. This output device can comprise a display, a lamp and/or an acoustic output device which can output any parameters or information detected by the apparatus accordingly to an operator.

Provision can also be made that the regulation/control is configured to verify the correct opening of a further valve, in particular of a manually operable hose clamp, with reference to a detected weight change. If, for example, a signal has been output to an operator to open a hose clamp and if a weight reduction of the solution bag is detected by the regulation/control, this can be interpreted by the apparatus as an indication that the hose clamp has actually been opened, whereby the verification of the opening takes place.

BRIEF DESCRIPTION OF THE DRAWINGS

Further details and advantages of the invention will be shown with reference to the Figures. There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
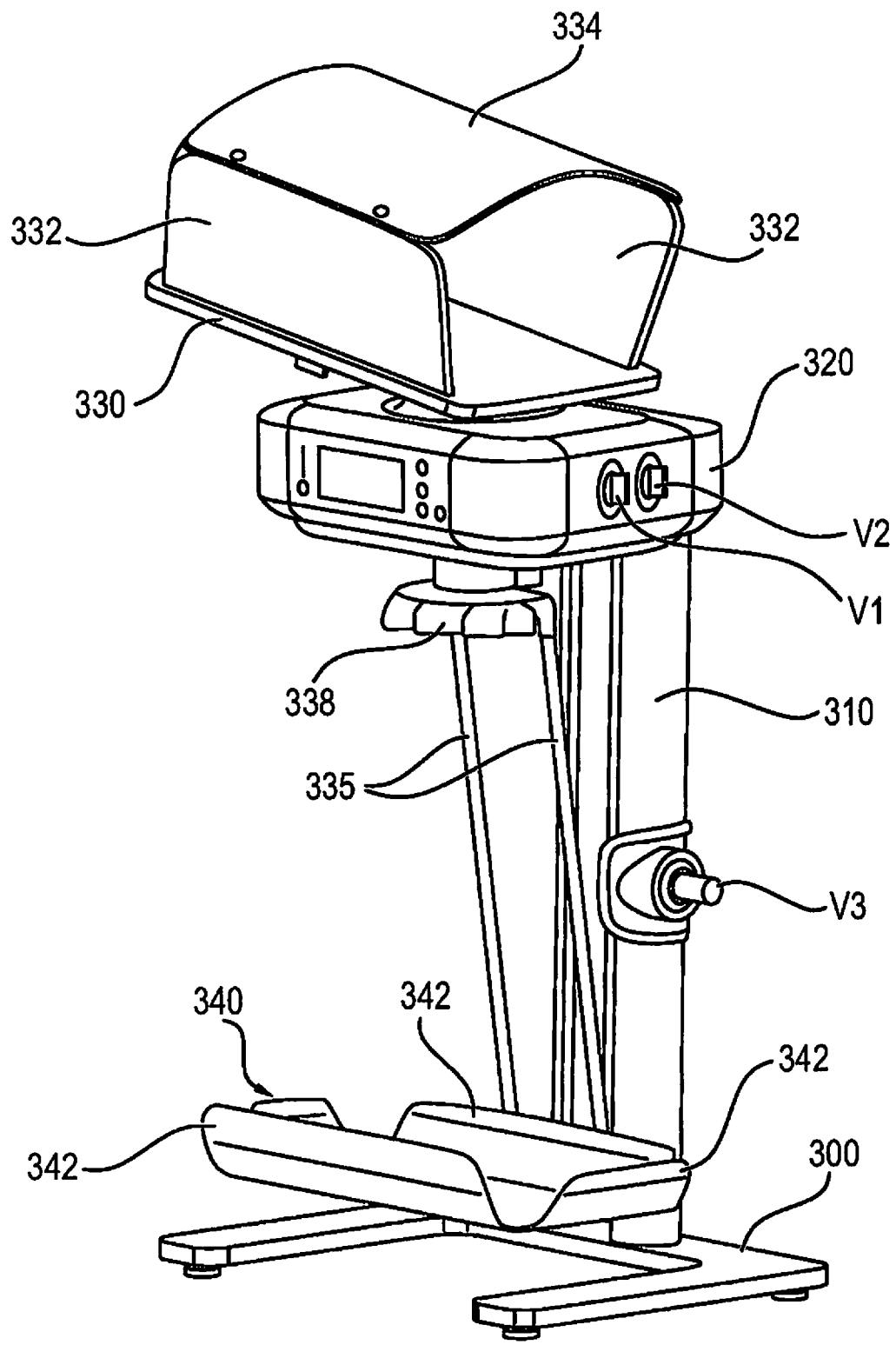
FIG. 1: a perspective view of an apparatus in accordance with the invention.

FIG. 1 shows a peritoneal dialysis machine in accordance with the present invention in a perspective view.

The peritoneal dialysis machine has a U-shaped pedestal 300 from which a machine housing support 310 extends vertically upwardly. The machine housing 320 is located at its upper end. The electronics required for operating the machine, such as control and regulation units, and the operating and/or display units, are located in the machine housing 320.

The heating pan 330 which serves the reception of solution bags containing fresh dialyzate to be supplied to the patient is arranged directly above the machine housing 320, directly connected thereto.

Rods 335 at which the weighing pan 340 is arranged are located at the bottom at the machine housing 320 or at the weighing pan or scale 338. The weighing pan 340 serves the reception of one or more receiving bags into which the used dialyzate coming from the patient moves.

As can be seen from FIG. 1, the weighing pan 340 is located directly above the floor on which the pedestal 300 of the peritoneal dialysis machine stands. It can furthermore be seen from FIG. 1 that the pedestal has a flat profile so that the weighing pan 340 can be arranged far to the bottom.

The spacing between the base of the weighing pan 340 and the floor amounts, for example, to a few cm, e.g. 5 cm to 10 cm, and preferably 7.5 cm to 8.5 cm.

The spacing between the base of the heating pan 330 and the base of the weighing pan 340 is preferably between 80 cm and 1.2 m.

The fluid control to and from the patient takes place via valves, wherein the valve or valves for the fluid connection between the solution bag or bags, which are located in the heating pan 330, and the patient are arranged at the machine housing 320. These valves are marked by the reference symbols V1, V2 in FIG. 1. The drainage valve V3, which is arranged between the patient and the receiving bag for consumed dialyzate, is located at the machine housing support 310. It is arranged at a height of approximately 40 cm to 50 cm, and preferably of 45 cm, above the floor. This allows a comfortable operation by the patient.

As can be seen from FIG. 1, the rods 335 extend from the rear side of the weighing pan 340 upwardly to the lower side of the machine housing 320. A good accessibility from the front side to the weighing pan 340 is thus present.

The rods 335 are arranged at a load cell or scale 338 which is located at or in the machine housing 320.

Both the heating pan 330 and the weighing pan 340 have a support surface for the bag or bags which is the base. Side walls 332 and 342 extend upwardly starting from the base. They have the object of holding the respective received bags securely in the pan. This is in particular of importance when a plurality of bags are received in the heating pan 330 and in the weighing pan 340.

The side walls 332 and 342 can be fastened by a plug-in connection or can be pivotable relative to the support surface so that the bags can be placed in and removed easily.

The heating pan 330 is furthermore provided with an upper cover 334 which has the object of keeping the heat, where possible, in the region of the solution bags which are located in the heating pan 330.

The hose system can be arranged in accordance with the invention such that it is not weighed by the weighing pan 340 or by the scale 338. For this purpose, it can be fastened to structures which are separate from the peritoneal dialysis machine so that the weight of the hose system does not act on the scale.

Figure 2:
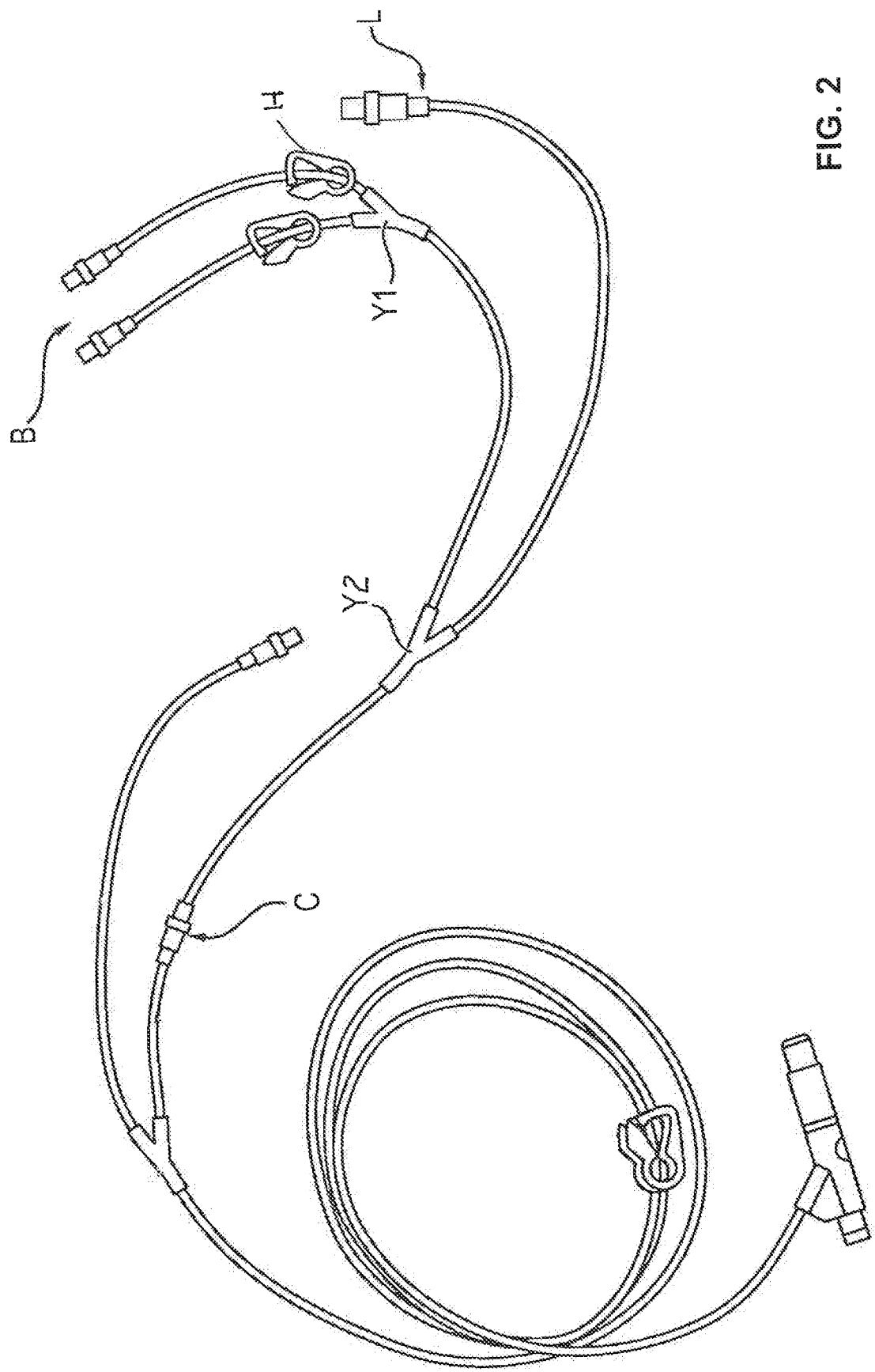
FIG. 2 a view of a hose system.

As can be seen from FIG. 2, the lines which are connected to the connectors B are connected via a Y piece Y1. The common line opening therefrom is connected via the further Y piece Y2 to the line which leads to the last bag.

The length of the line section between the connector C and the Y piece "Y2" is preferably in the range from 3 cm to 7 cm, the length of the line section between the Y piece "Y2" and the Y piece "Y1" is preferably in the range from 15 cm to 25 cm, and the length of the line section between the Y piece "Y2" and the connector L is preferably in the range between 40 cm and 50 cm, and the length of the line section between the Y piece "Y1" and the connectors B is preferably in the range between 15 cm and 25 cm.

Figure 3:
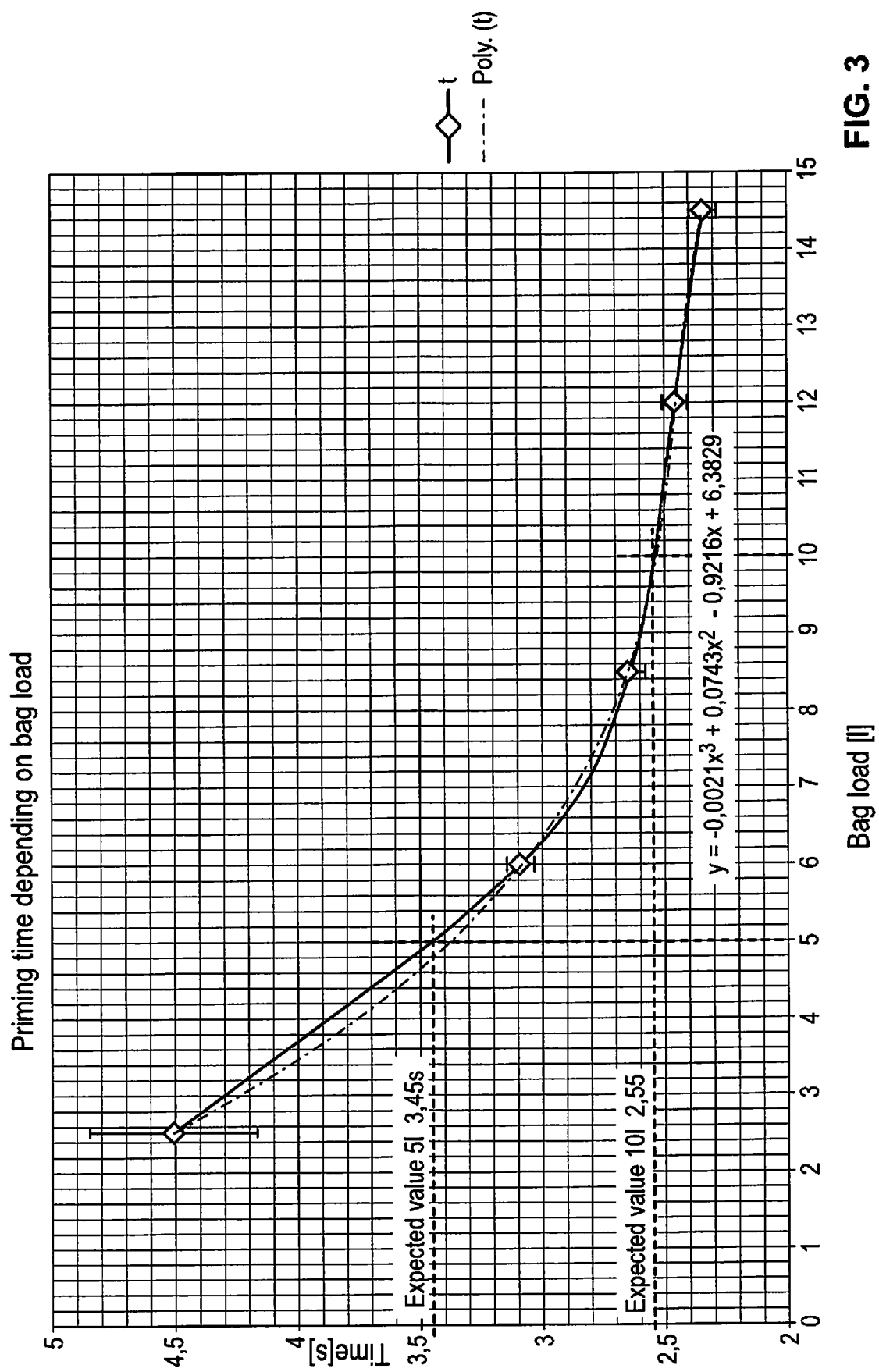
FIG. 3: a characteristic curve shown by way of example.

FIG. 3 shows a characteristic shown by way of example in which the weight can be stored on the abscissa and the opening duration of the valves can be stored on the ordinate.

The invention can provide that an opening time of the valves can be determined in dependence on the weight placed on the scale by means of a characteristic with reference to the variable weight change during the fluid removal up to the complete filling of the patient line to ensure a state free of air in the patient line.

Figure 4:
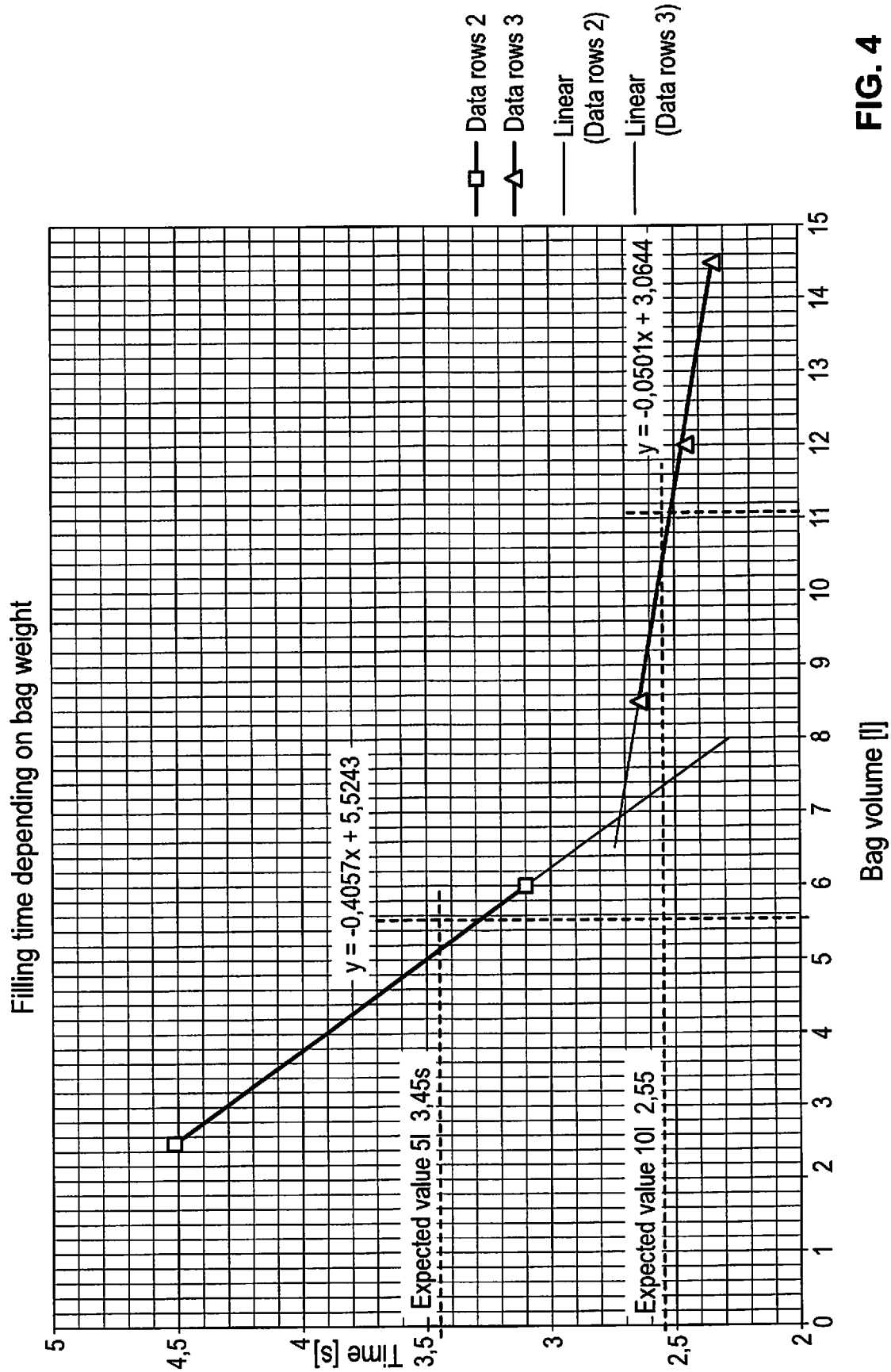
FIG. 4: a linearized characteristic shown by way of example.

FIG. 4 shows a characteristic with linearized data rows.

For this purpose, all the valves are first opened (bag valves and drainage valves) to flush possible particles, which may e.g. stem from the opening of the snap-off cones, and air into the drainage bag. The patient is subsequently prompted to open the hose clamp to the patient line to flush the latter. At the same time, a user-caused incorrect operation can be recognized by the idea in accordance with the invention.

This is in particular often difficult to ensure with units which are operated without any great technical equipment since specific process routines are the responsibility of the user/patient. Increased patient safety is therefore in particular desirable for the application in the home area. A proper opening of the dialysis bag connectors can be checked using the invention in a further embodiment. In this respect, first only the two hose valves (V1, V2) are opened to allow the dialysis fluid to flow up to the drainage valve. The drainage valve (V3) remains closed.

The fluid thus remains in the hose kit. A new static balance is adopted behind the scale. A weight change can now be determined since the fluid which has flowed out has not yet reached the drainage bag on the drain pan which is likewise connected to the one load cell. A conclusion can thus be drawn on a fluid flow which has taken place via the weight change of the dialyzate bags on the weighing pan and a conclusion can thus be made whether the bag connectors and/or hose clamps H were opened or whether an improper condition is present.

In a further embodiment, the drainage valve V3 can be briefly opened until a fluid flow is recognized and before the fluid has reached the drainage pan or the drainage bag. If it was found in a first step that the bag connectors and/or the hose clamps have been properly opened, a check can be made in a second step whether the hose clamp to the drainage bag is open. The hose valves V1 and/or V2 and also the drainage valve V3 are opened for this purpose. If a weight change can now be recognized between the last measurement (weight change due to fluid flow in the hose system) and the measurement (fluid from the hose system in the drainage bag), this allows the conclusion that the hose clamp to the drainage bag is also open.

It is conceivable to attach a fluid reservoir to the drainage hose to be able to determine the cloudiness of the drain fluid.

Disadvantages of existing methods or apparatus are that the patient has to monitor the flushing process, has to operate valves manually and has to react fast on closing the valves. The known methods and apparatus are thus prone to error, require a higher patient effort and provide less patient comfort.

Advantages of the invention are, conversely, that a flushing can be carried out automatically and the treatment is thus less prone to error or to the introduction of air, for non-fractured cones of the solution bags.

An overfilling of the patient line and thus a running of the dialyzate out of the pierced protective cap of the patient connector can be avoided, whereby a contamination of the patient connector and peritonitis can be avoided.

In accordance with the invention, the weight change on the start of the priming of the tubing or of the flushing can be recognized and the user can be alerted immediately if the priming cannot be started.

It can furthermore be recognized in accordance with the invention whether a filling of the patient line can be started and an alert can be given if a filling of the patient line is not possible.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A method for the automatic, weight-dependent flushing or filling of a hose system for a gravimetric cycler for peritoneal dialysis, wherein the gravimetric cycler contains a bag of fresh dialysate and a drainage bag below the bag of fresh dialysate, the gravimetric cycler comprises the hose system, a scale, a regulation/control, a bag valve, and a drainage valve, and the hose system includes a first line section for connection to the drainage bag, a second line section for connection to the bag of fresh dialysate, and a third line section for connection to a patient, the method comprising:
    measuring a weight of the bag of fresh dialysate, with the scale; and
    opening, for an opening duration, the bag valve and the drainage valve, wherein the opening duration is derived from the measured weight of the bag of fresh dialysate, and from an opening duration stored in the regulation/control, wherein the opening duration corresponds to the measured weight of the bag of fresh dialysate, and the opening of the bag valve and of the drainage valve is actuated based on an opening signal sent from the regulation/control to the bag valve and to the drainage valve.

2. The method in accordance with claim 1, wherein the method includes detecting whether the bag valve and the drainage valve have been opened by measuring a weight change with the scale.

3. The method in accordance with claim 1, wherein the method includes detecting a weight reduction of the bag of fresh dialysate during the opening of the bag valve and the drainage valve, by using the scale, and modifying the opening duration in dependence on the detected weight reduction.

4. The method in accordance with claim 1, wherein the method includes, after closing the bag valve and the drainage valve, issuing a prompt is issued to an operator to open a hose clamp, with dialysate being conducted in a direction of a connector.

5. The method in accordance with claim 4, wherein the method includes detecting whether the hose clamp has been opened, by using the scale.

6. The method in accordance with claim 5, wherein the method includes opening a hose valve as well as the drainage valve; and determining that a hose clamp on the first line section is open when there is a weight change between a measurement of weight change due to fluid flow in the hose system, and a measurement of fluid from the hose system into the drainage bag.

7. The apparatus in accordance with claim 1, further comprising using the scale to detect a combined weight of the drainage bag and the bag of fresh dialysate.

8. An apparatus for automatic, weight-dependent filling of a hose system for a gravimetric cycler for peritoneal dialysis, wherein
    the gravimetric cycler contains a bag of fresh dialysate and a drainage bag below the bag of fresh dialysate, the gravimetric cycler comprises the hose system, a scale, a regulation/control, a bag valve, and a drainage valve,
    the hose system includes a first line section for connection to the drainage bag, a second line section for connection to the bag of fresh dialysate, and a third line section for connection to a patient,
    the scale is configured to measure a weight of the bag of fresh dialysate,
    the regulation/control unit has stored therein different opening durations corresponding to different weights of bags of fresh dialysate,
    the regulation/control unit is configured to control opening of the bag valve and the drainage valve, and
    the regulation/control unit is further configured to derive the opening duration of the bag valve and the drainage valve from the stored opening duration that corresponds to the weight of the bag of fresh dialysate as measured by the scale.

9. The apparatus in accordance with claim 8, wherein the regulation control unit is configured to open the bag valve and/or the drainage valve in dependence on the weight of the bag of fresh dialysate.

10. The apparatus in accordance with claim 8, wherein the regulation/control unit is configured to verify correct opening of the bag valve and/or the drainage valve with reference to a detected weight change of the weight of the bag of fresh dialysate.

11. The apparatus in accordance with claim 8, wherein the apparatus further comprises an output device configured for outputting information to an operator.

12. The apparatus in accordance with claim 8, wherein the regulation/control unit is configured to verify correct opening of a further valve on the first line section, with reference to a detected weight change of the weight of the bag of fresh dialysate.

13. The apparatus in accordance with claim 12, wherein the further valve is a manually operable hose clamp.

14. The apparatus in accordance with claim 8 in combination with a peritoneal dialysis machine.

15. The apparatus in accordance with claim 8, wherein the scale detects a combined weight of the drainage bag and the bag of fresh dialysate.

* * * * *